US00PP08273P

United States Patent [19]

Fruehwirth

[11] Patent Number: Plant 8,273

[45] Date of Patent: Jun. 22, 1993

[54] POINSETTIA NAMED '268 MARBLE'

[75] Inventor: Franz Fruehwirth, Encinitas, Calif.

[73] Assignee: Paul Ecke Ranch, Inc., Encinitas, Calif.

[21] Appl. No.: 730,194

[22] Filed: Jul. 15, 1991

[51] Int. Cl.[5] ..... A01H 5/00

[52] U.S. Cl. ..... Plt./86.1

[58] Field of Search ..... Plt./86.1–86.4

[56] References Cited

U.S. PATENT DOCUMENTS

P.P. 7,275 7/1990 Fruehwirth ..... Plt. 86.3

*Primary Examiner*—James R. Feyrer

*Attorney, Agent, or Firm*—Arnold, White & Durkee

[57] ABSTRACT

This new Poinsettia cultivar, designated '268 Marble', is a vigorous plant with large, erect, bicolored pink and white flower bracts. Cultivar '268 Marble' is a sport of the red bracted cultivar '268' (U.S. Plant Pat. No. 7,275). '268 Marble', like its parent '268', is unique because the flower bracts remain erect and do not droop, even after commercial shipping and handling or as the flowers mature. It always looks "fresh" which adds to its beauty and increases its value as a consumer product. Poinsettia '268 Marble' has the same flowering response time and cultural requirements as its parent '268'.

1 Drawing Sheet

BACKGROUND OF THE INVENTION

This new Poinsettia cultivar originated as a color sport of '268' (U.S. Plant Pat. No. 7,275) in a greenhouse in Encinitas, Calif. Color sports were induced through irradiation of vegetative plants with 4000 rads of radiation. It was selected from many plants because of its large, erect and bicolored, pink and white flower bracts and self-branching traits which distinguish it from other poinsettia cultivars, and seem to make it a desirable plant for commercial greenhouse production. After selection, vegetative reproduction of this plant was accomplished by stem cuttings for test purposes in Encinitas, Calif., and clones of the plant were subjected to successive generations of vegetative propagation which demonstrated that its distinct characteristics hold true from generation to generation.

DESCRIPTION OF THE PHOTOGRAPHS

Poinsettia '268 Marble' is illustrated in the accompanying color photographs. The upper photo is a side view of one pinched '268 Marble' plant in a 14 cm. pot. The lower photo is a top view of the same plant showing flower and bract formation.

DESCRIPTION OF THE PLANT

The following is a detailed description of this new Poinsettia as observed in my greenhouse in Encinitas, Calif., during December, 1990. Observations from flowering plants, grown as potted pinched plants, were recorded. The pot was 14 cm. in diameter and 11 cm. in height. Color designations were compared to the 1986 edition of R.H.S. Colour Chart, first published in 1966 by The Royal Horticultural Society, London, England.

THE PLANT

Origin: Sport of '268' (U.S. Plant Pat. No. 7,275).

Classification:

*Botanic.*—*Euphorbia pulcherrima* Willd.

*Common name.*—Poinsettia.

*Cultivar name.*—'268 Marble'.

Form: Shrub.

Height: Short to medium.

Growth habit: As a single stemmed plant, upright and vigorous with many self-branching axillary stems. The application of a chemical growth retardant may not be needed to restrict height for commercial pot plant production. Observations of single, pinched plants in pots with an overall height of 35 cm. and an overall width of 48 cm. were made. The bract diameter of individual flowers was 26 cm.

Branching: Poinsettia '268 Marble', like its parent plant '268', has self-branching traits. Branching can be enhanced by removal of the stem tip. Then, several flowering branches with equal vigor will develop on a single plant.

Growth rate: Very fast. Rooting of stem cuttings occurs in 12–18 days under intermittent mist. The plant will flower in about nine weeks under continuous long night conditions and night temperatures of about 16–18 degrees C.

Foliage: The foliage is clean and uniformly green from bottom to top of the plant. The leaves are of medium size, leaf blades typically being 12–13 cm. long and 9–10 cm. wide and with leaf petioles 5–7 cm. long.

*Leaf shape.*—Typical leaves are ovate with obtuse bases and acuminate tips. Leaf margins are mostly entire with slight lobing on each side of some leaf blades. The bract-like leaves of intermediate coloration have a somewhat creamy color with respect to the color of the full bracts, near RHS 5C, with generally a pronounced green color, near RHS 147A, radiating along the veins which extend laterally from the midrib of each bract-like leaf.

*Color.*—Upper side — Green, near RHS 147A. Under side — Near RHS 147B.

*Retention.*—The foliage lasts fairly well even under low light intensities in the consumer's home.

Bracts: Generally there are 15–18 uniformly colored bracts of various sizes subtending the cyathia. The primary bracts have blades typically 15–17 cm. long and 11–13 cm. wide and petioles 3–4 cm. long. Bract attitude is erect for both '268 Marble' and its parent '268' bract shapes, sizes and color patterning are widely variable, and present an appealing contrast to the deep green foliage.

*Shape.*—Bracts are mostly ovate, but elliptic for smaller bracts, with acute bases and acuminate tips. Primary bracts are lobed with two indentations on either side of the bract. Secondary bracts have entire margins.

*Color.*—Upper side — Bicolored: pink and creamy white on each bract. An irregular area of pink, between RHS 48B and RHS 48C but nearer RHS 48C, is located at the center of the bracts, usually on either side of the mid-vein. The bracts have an essentially white to creamy white colored marginal variegation darker than RHS 155A and near RHS 4D around the pink patterns of the central area of the bracts. The pink bract pattern is characteristically random, but principally central within the top and bottom surfaces of each bract. Furthermore, the pink coloration is not uniform but laminated in appearance. The intensity of the pink patterns is darker in some bracts as compared to other bracts, which may be due to lamination of mesophyll cells of different pigment content.

The lateral veins extending from the midrib of each bract are generally not pigmented with red, and are instead generally creamy white. This creates a subtle herring-bone effect to the vein pattern. Under side — Bicolored: Pink and creamy white. The pattern of each color mirrors the upper surface. The pink is between RHS 48B and RHS 48C, but nearer RHS 48C. The peripheral creamy white is darker than RHS 155A and near RHS 4D.

Flowers: Generally, 12–15 cyathia (flowers) are present when the plant is in full bloom. Each cyathium is 6–7 mm long and 4–5 mm wide, green in color, and fringed with yellow at the distal end. One yellow nectar cup protrudes from the side of each cyathium. The flower pedicel is also green and about 5–6 mm in length. The stamens protruding from the cyathia are pink. There are typically 12–15 bifurcated anthers ripening at any one time. The pollen produced is yellow and copious. Flowers are self-incompatible and thus no viable seed is formed without cross-pollination. Poinsettia '268 Marble' is similar in appearance to Poinsettia 'C-27 Marble' (U.S. Ser. No. 07/730,349), except that Poinsettia '268 Marble' of the present invention is self-branching, whereas 'C-27 Marble' is not self branching. Furthermore, '268 Marble' generally has 15–18 uniformly colored bracts of various sizes subtending the cyathia, as distinguished from the 'C-27 Marble' Poinsettia, which have generally 18–24 bracts subtending the cyathia.

What is claimed is:

1. A new and distinct Poinsettia cultivar, substantially as herein shown and described, characterized by its large bicolored pink and white, erect flower bracts, and self-branching traits.

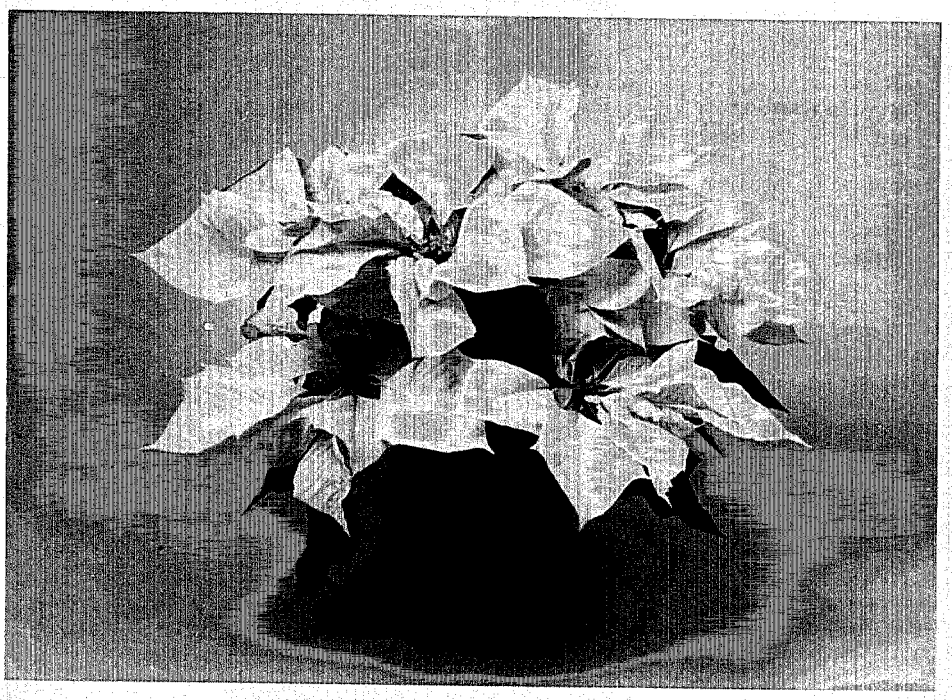
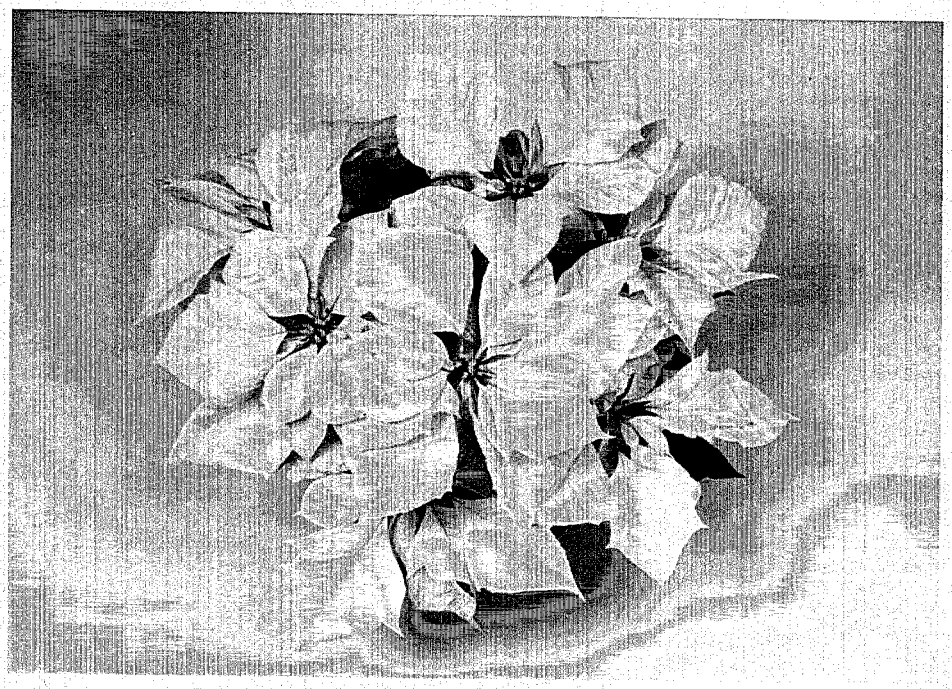

* * * * *